(12) United States Patent
Ziegler (10) Patent No.: US 11,727,826 B2
(45) Date of Patent: Aug. 15, 2023

(54) RESUSCITATION TRAINING DEVICE AND METHOD OF USE

(71) Applicant: Ryan Ziegler, Running Springs, CA (US)

(72) Inventor: Ryan Ziegler, Running Springs, CA (US)

( * ) Notice: Subject to any disclaimer, the term of this patent is extended or adjusted under 35 U.S.C. 154(b) by 567 days.

(21) Appl. No.: 16/807,109

(22) Filed: Mar. 2, 2020

(65) Prior Publication Data

US 2021/0272477 A1 Sep. 2, 2021

(51) Int. Cl.
| | |
|---|---|
| *G09B 23/28* | (2006.01) |
| *A61M 16/06* | (2006.01) |
| *A61M 16/00* | (2006.01) |
| *A61M 16/20* | (2006.01) |
| *A61M 16/04* | (2006.01) |
| *A61M 16/08* | (2006.01) |
| *A41D 13/11* | (2006.01) |

(52) U.S. Cl.
CPC ....... *G09B 23/288* (2013.01); *A61M 16/0084* (2014.02); *A61M 16/04* (2013.01); *A61M 16/0605* (2014.02); *A61M 16/0833* (2014.02); *A61M 16/0866* (2014.02); *A61M 16/20* (2013.01); *A41D 13/11* (2013.01); *A61M 16/0078* (2013.01); *A61M 16/06* (2013.01); *A61M 16/208* (2013.01); *A61M 2016/0027* (2013.01); *A61M 2205/583* (2013.01)

(58) Field of Classification Search
CPC .............. A61M 16/00; A61M 16/0048; A61M 16/0057; A61M 16/0078; A61M 16/0084; A61M 16/04; A61M 16/0463; A61M 16/06; A61M 16/0816; A61M 16/0833; A61M 16/0866; A61M 16/20; A61M 16/208

See application file for complete search history.

(56) References Cited

U.S. PATENT DOCUMENTS

| | | | |
|---|---|---|---|
| 3,276,147 | A | 10/1966 | Padellford |
| 4,491,423 | A | 1/1985 | Cohen |
| 4,532,923 | A | 8/1985 | Flynn |
| 5,363,842 | A | 11/1994 | Mishelevich et al. |

(Continued)

FOREIGN PATENT DOCUMENTS

| | | |
|---|---|---|
| EP | 2606820 A1 | 6/2013 |
| WO | 2001015761 A1 | 3/2001 |

(Continued)

OTHER PUBLICATIONS

Nimbalka, et al., Comparison of efficacy of three devices of manual positive pressure ventilation: a mannequin-based study, Italian Journal of Pediatrics, Mar. 31, 2015, 5 pages.

(Continued)

*Primary Examiner* — Joseph D. Boecker
(74) *Attorney, Agent, or Firm* — Fulwider Patton LLP (57) ABSTRACT

A resuscitation training device attaches to an air delivery ventilation device to determine if there is a proper mask seal between a live training subject or a training manikin. A pressure sensor attached to the resuscitation training device provides instant feedback to determine if there is a proper seal. The resuscitation training device includes a tubular member having an air metering orifice in fluid communication with the mask and the pressure sensor.

20 Claims, 7 Drawing Sheets

(56) References Cited

U.S. PATENT DOCUMENTS

| | | |
|---|---|---|
| 5,722,394 A | 3/1998 | Loescher |
| 5,839,430 A | 11/1998 | Cama |
| 5,922,610 A | 7/1999 | Alving et al. |
| 5,996,579 A | 12/1999 | Coates et al. |
| 6,567,686 B2 | 5/2003 | Sexton et al. |
| 6,792,947 B1 | 9/2004 | Bowden |
| 7,347,201 B2 | 3/2008 | Djupesland |
| 8,631,790 B1 | 1/2014 | Di Capua et al. |
| 8,905,034 B2 | 12/2014 | Goranov et al. |
| 9,138,169 B2 | 9/2015 | Beard |
| 9,446,211 B2 | 9/2016 | Varga et al. |
| 10,029,056 B2 | 7/2018 | Reilly et al. |
| 10,182,966 B2 | 1/2019 | Freeman et al. |
| 10,639,436 B2 | 5/2020 | Chatham |
| 10,677,094 B2 | 6/2020 | Uhkötter et al. |
| 2004/0094150 A1* | 5/2004 | Flynn ............... A61M 16/0057 128/202.28 |
| 2005/0133024 A1 | 6/2005 | Coifman |
| 2006/0060199 A1 | 3/2006 | Lampotang et al. |
| 2008/0236585 A1* | 10/2008 | Parker ............... A61M 16/10 128/205.23 |
| 2012/0315614 A1 | 12/2012 | Krauza |
| 2013/0081616 A1* | 4/2013 | Tatkov ............... A61M 16/0816 128/201.13 |
| 2015/0096559 A1 | 4/2015 | Duval-Arnould et al. |
| 2015/0297118 A1 | 10/2015 | Löndahl et al. |
| 2017/0049978 A1 | 2/2017 | Berg et al. |

FOREIGN PATENT DOCUMENTS

| | | |
|---|---|---|
| WO | 2005123165 A1 | 12/2005 |
| WO | 2010059049 A2 | 5/2010 |
| WO | 2015144500 A1 | 10/2015 |

OTHER PUBLICATIONS

Dr. O'Donnell et al., Neonatal resuscitation 2: an evaluation of manual ventilation devices and face masks, PubMed, May 4, 2005, 2 pages.

Van Vonderen, et al., Two-Minute Training for Improving Neonatal Bag and Mask Ventilation, PubMed, Oct. 3, 2014, 2 pages.

Dr. O'Donnell et al.. Neonatal Resuscitation 1: a Model to Measure Inspired and Expired Tidal Volumes and Assess Leakage at the Face Mask, www.archdischild.com, May 4, 2005, 4 pages.

\* cited by examiner

RESUSCITATION TRAINING DEVICE AND METHOD OF USE

BACKGROUND

In the art of manual air delivery systems for ventilation, a bag valve mask (BVM) has been the primary method of ventilating a human patient who is in respiratory arrest or is otherwise incapable of breathing independently. The BVM is well-known in the art. Several other devices, including but not limited to, pocket masks, face shields, endotracheal tubes, resuscitors, and ventilators are also used to facilitate the delivery of breathing air to a person incapable of independent breathing. In all of these devices, the skill and training of the operator determines the efficacy of ventilation. If the operator does not properly fit the manual air delivery system over the applicable airway, then the patient would not receive the air required for proper ventilation. Additionally, the operator's failure to deliver the correct volume of air or ventilation rate can cause gastric distention and aspiration of stomach contents in the patient, which may in some circumstances lead to death. This is why proper training before using such manual resuscitation devices in real life is necessary and important.

Current training with manual air delivery ventilation systems does not allow an operator to receive feedback on whether the operator has properly placed the device and made a seal over the airway sufficient to cause the subject to receive the necessary air through external positive pressure. As a result, the first time an individual operates a BVM (or another manual air delivery ventilation system) in a non-training environment the operator usually places the device incorrectly and has to adjust it several times. Because BVMs (and other manual air delivery ventilation system) are commonly used in emergency care and critical care situations in which timing is of the essence, having operators that are well-skilled in their technique will lead to better patient outcomes. What is needed in the art of manual air delivery ventilation systems is a device that is easy to attach to existing systems and which provides measurable feedback to the operator about his or her technique in the training environment so that the operator can perfect his or her technique in such environment before using such system in an emergency situation.

SUMMARY OF THE INVENTION

A resuscitation training device is attached to an air delivery ventilation device to determine whether there is a proper mask seal between a live training subject or a training manikin.

In one embodiment, a resuscitation training device includes a first tubular member having a first end and a second end and a tubular body extending between the first and second ends. A second tubular member has a first end and second end, where the second end is attached to the tubular body of the first tubular member. A first lumen extends from the first end of the first tubular member to an orifice plate and a second lumen extends through the second tubular member and is in fluid communication with the first lumen. There is a metering orifice on the orifice plate, the metering orifice being in fluid communication with both the first lumen and the second lumen. There is a third lumen extending from the metering orifice to the second end of the first tubular member. A pressure sensing device is attached to the second tubular member in order to determine whether there is a proper seal between the mask and a live training subject or a training manikin. In one embodiment, the pressure sensing device is an elastic member, such as a balloon, that will inflate if there is a proper seal between the mask and the live training subject or the training manikin. If there is a leak between the mask and the training subject or training manikin, the balloon will not inflate, giving the operator instant feedback on the proper placement of the mask. The resuscitation training device can be used with any of a BVM, a pocket mask, a face shield, an endotracheal tube, a resuscitator, and a ventilator. The diameter of the metering orifice can vary in order to match the sensitivity of the pressure sensing device. By way of example, the diameter of the metering orifice can range from 0.039 inch to 0.24 inch (1 mm to 6 mm), depending on the type of pressuring sensing device being used. The metering orifice diameter can even change with the use of different balloons having different elasticities. In one embodiment, the pressure sensing device provides a digital readout to determine whether there is a proper seal between the mask and the live training subject or the training manikin.

In another embodiment, a resuscitation training assembly includes an air delivery ventilation device, such as a BVM, a pocket mask, a face shield, an endotracheal tube, a resuscitator, and a ventilator. In this embodiment, a first tubular member has a first end and a second end and a tubular body that extends between the first end and the second end. A second tubular member has a first end and a second end, whereby the second end is attached to the tubular body of the first tubular member. The first end of the first tubular member is attached to the air delivery ventilation device. A first lumen extends from the first end of the first tubular member to an orifice plate and a second lumen extends through the second tubular member and is in fluid communication with the first lumen. A metering orifice is on the orifice plate, and is in fluid communication with the first lumen and the second lumen. There is a third lumen extending from the metering orifice to the second end of the first tubular member. A pressure sensing device is attached to the second tubular member. The first tubular member is attached to the air delivery ventilation device so that when a person uses the air delivery ventilation device to deliver air, the pressure sensing device provides instantaneous feedback to the person to determine if there is a proper seal between the air delivery ventilation device and the human patient or training manikin. The pressure sensing device provides instantaneous manual, analog or digital feedback to determine whether there is a proper mask seal between the live training subject or a training manikin. The diameter of the metering orifice can vary in order to match the sensitivity of the pressure sensing device. By way of example, the diameter of the metering orifice can range from 0.039 inch to 0.24 inch (1 mm to 6 mm), depending on the type of pressuring sensing device being used. The metering orifice diameter can even change with the use of different balloons having different elasticities.

The resuscitation training device can be formed of a durable plastic material that is injection molded or formed on a 3D printer. Alternatively, the device can be formed from other materials including metallic alloys such as stainless steel, titanium, and cobalt-chromium, as examples. The resuscitation training device also can be made of softer plastic materials such as silicone in order to enhance a better seal with the attachment to the mask and the valve. It is contemplated that the resuscitation training device be formed as a unitary structure, however, it is envisioned that the component parts can be formed and attached together to form the device.

DETAILED DESCRIPTION OF THE PREFERRED EMBODIMENTS

A resuscitation training device is attached to an air delivery ventilation device to determine whether there is a proper mask seal between a live training subject or a training manikin.

In one embodiment, as shown in FIGS. 1-7, an air delivery ventilation device 10, such as bag valve mask (BVM) 12 is used as a training device on a live training subject or a training manikin. The BVM 12 includes a valve 13, an air bag 16 and a mask 14. A resuscitation training device 18 is attached to the BVM 12 between the valve 13 and the mask 14. The resuscitation training device 18 includes a first tubular member 22 having a first end 24 and a second end 26 and a tubular body 28 extending between the first and second ends. A second tubular member 30 has a first end 32 and second end 34, where the second end 34 is attached to the tubular body 28 of the first tubular member 22. A first lumen 36 extends from the first end 24 of the first tubular member 22 to an orifice plate 38 and a second lumen 40 extends through the second tubular member 30 and is in fluid communication with the first lumen 36. There is a metering orifice 42 on the orifice plate 38, the metering orifice 42 being in fluid communication with both the first lumen 36 and the second lumen 40. There is a third lumen 44 extending from the metering orifice 42 to the second end 26 of the first tubular member 22. A pressure sensing device 50 is attached to the second tubular member 30 in order to determine whether there is a proper seal between the mask 14 and a live training subject or a training manikin. The first end 24 of the first tubular member 22 comprises an air inlet 25 that is removably attached to the valve 13 using any type of air tight connection (e.g., an adapter fitting having a variable diameter that can be used with any air delivery ventilation device). Alternatively, an air tight seal can be formed by wrapping silicone adhesive tape that is pliable around the joint, providing an air tight seal, and it is easily removable. The second end 26 of the first tubular member 22 comprises an air outlet 27 that is removably attached to the mask 14, again using any suitable type of air tight connection. The first end 32 of the second tubular member 30 is comprises an air outlet 33 that removably attached to the pressure sensing device 50 (e.g., balloon 20). In one embodiment, the pressure sensing device 50 is an elastic member, such as a balloon 20, that will inflate if there is a proper seal between the mask 14 and the live training subject or the training manikin. If there is a leak between the mask 14 and the training subject or training manikin, the balloon 20 will not inflate, giving the operator instant feedback on the proper placement of the mask. The resuscitation training device 18 can be used with any of a BVM, a pocket mask, a face shield, an endotracheal tube, a resuscitator, and a ventilator. In one embodiment, the pressure sensing device 50 (FIG. 5) provides a digital readout to determine whether there is a proper seal between the mask 14 and the live training subject or the training manikin. The diameter of the metering orifice can vary in order to match the sensitivity of the pressure sensing device. By way of example, the diameter of the metering orifice can range from 0.039 inch to 0.24 inch (1 mm to 6 mm), depending on the type of pressuring sensing device being used. The metering orifice diameter can even change with the use of different balloons having different elasticities. In one embodiment, the pressure sensing device provides an analog readout or a digital readout to determine whether there is a proper seal between the mask and the live training subject or the training manikin.

Figure 1:
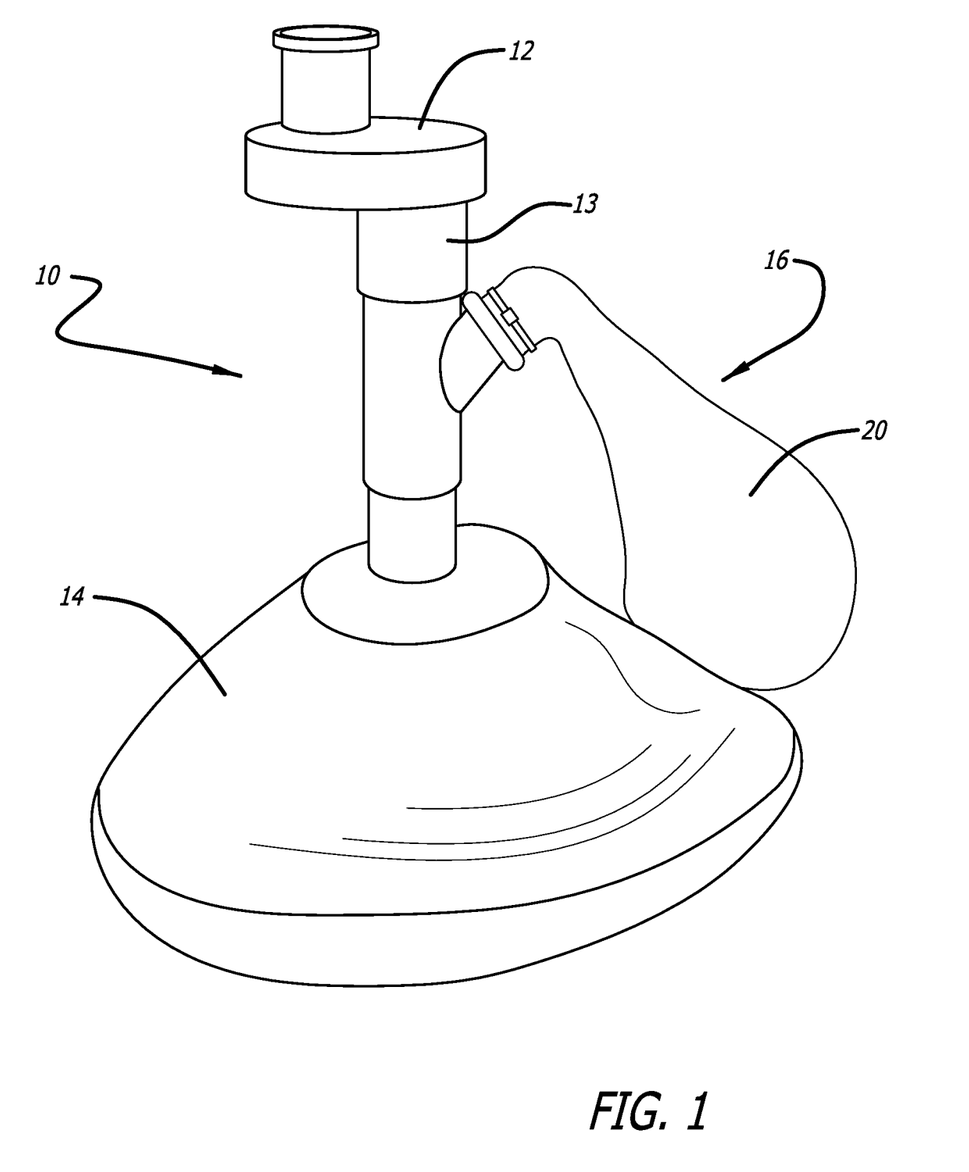
FIG. 1 is a schematic view of a BVM depicting a resuscitation training device attached to the valve and the mask.
Figure 2:
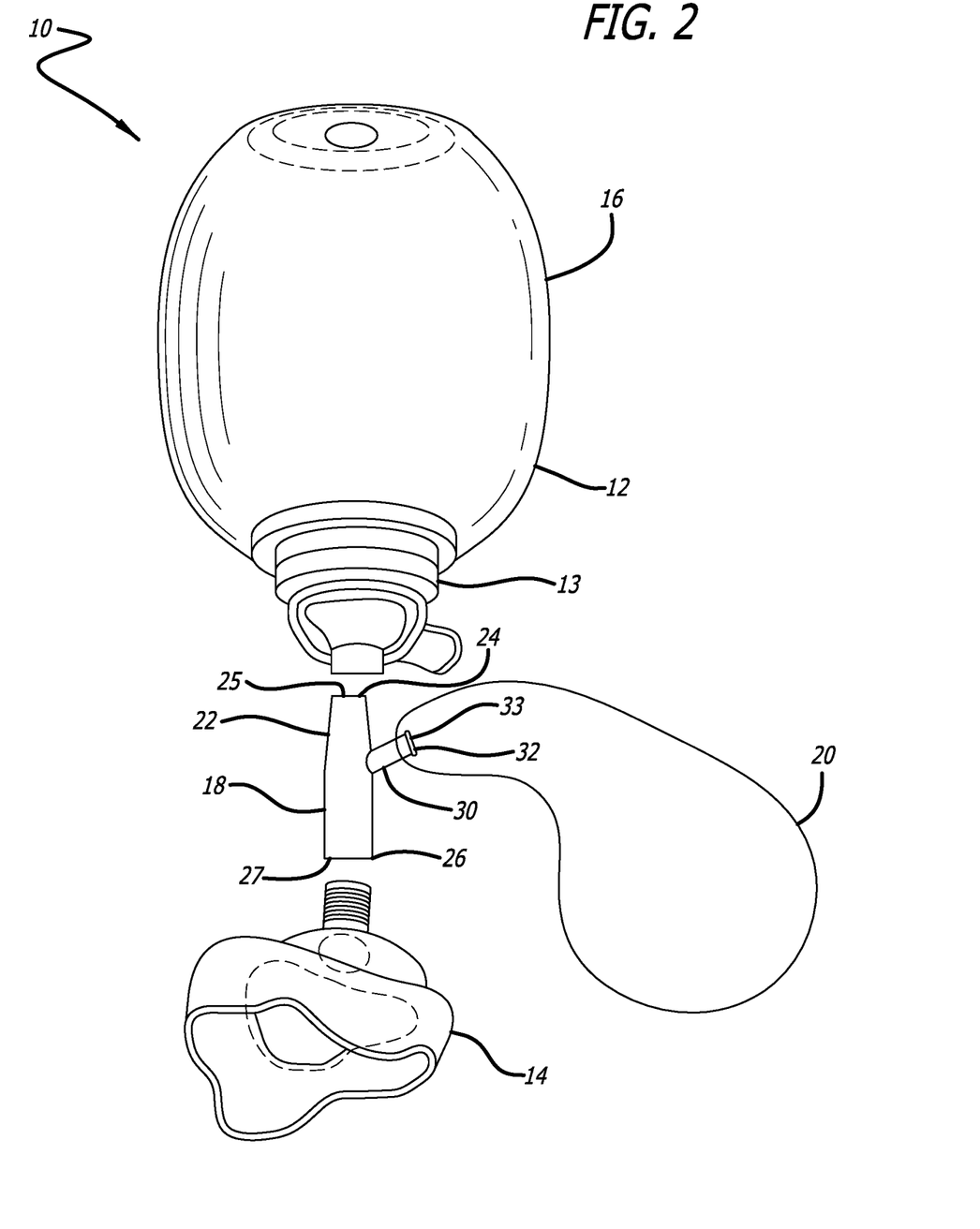
FIG. 2 is an exploded view of a BVM depicting the resuscitation training device prior to being connected to the valve and mask.
Figure 3:
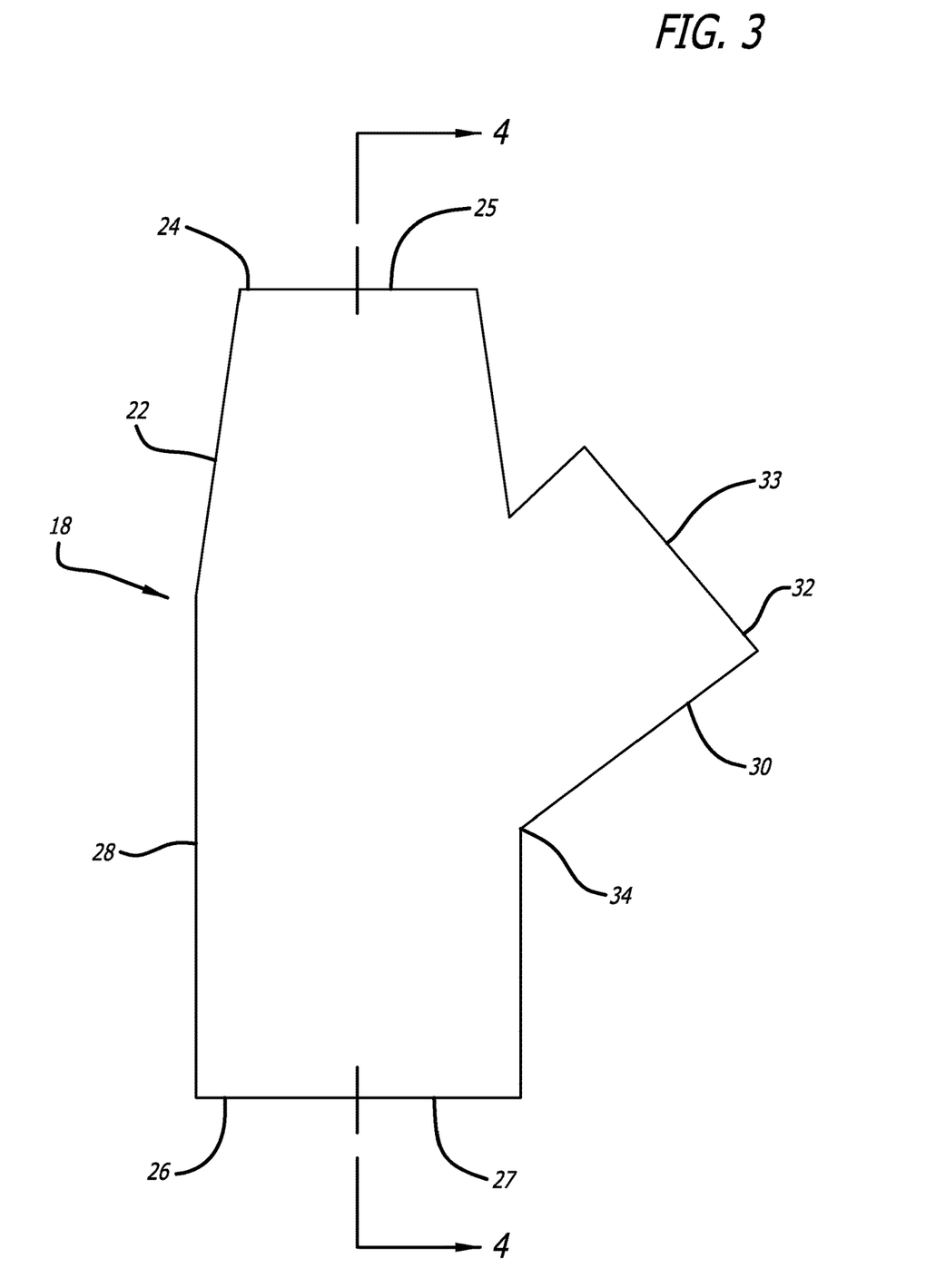
FIG. 3 is a plan view of the resuscitation device depicting the first and second tubular members.
Figure 4:
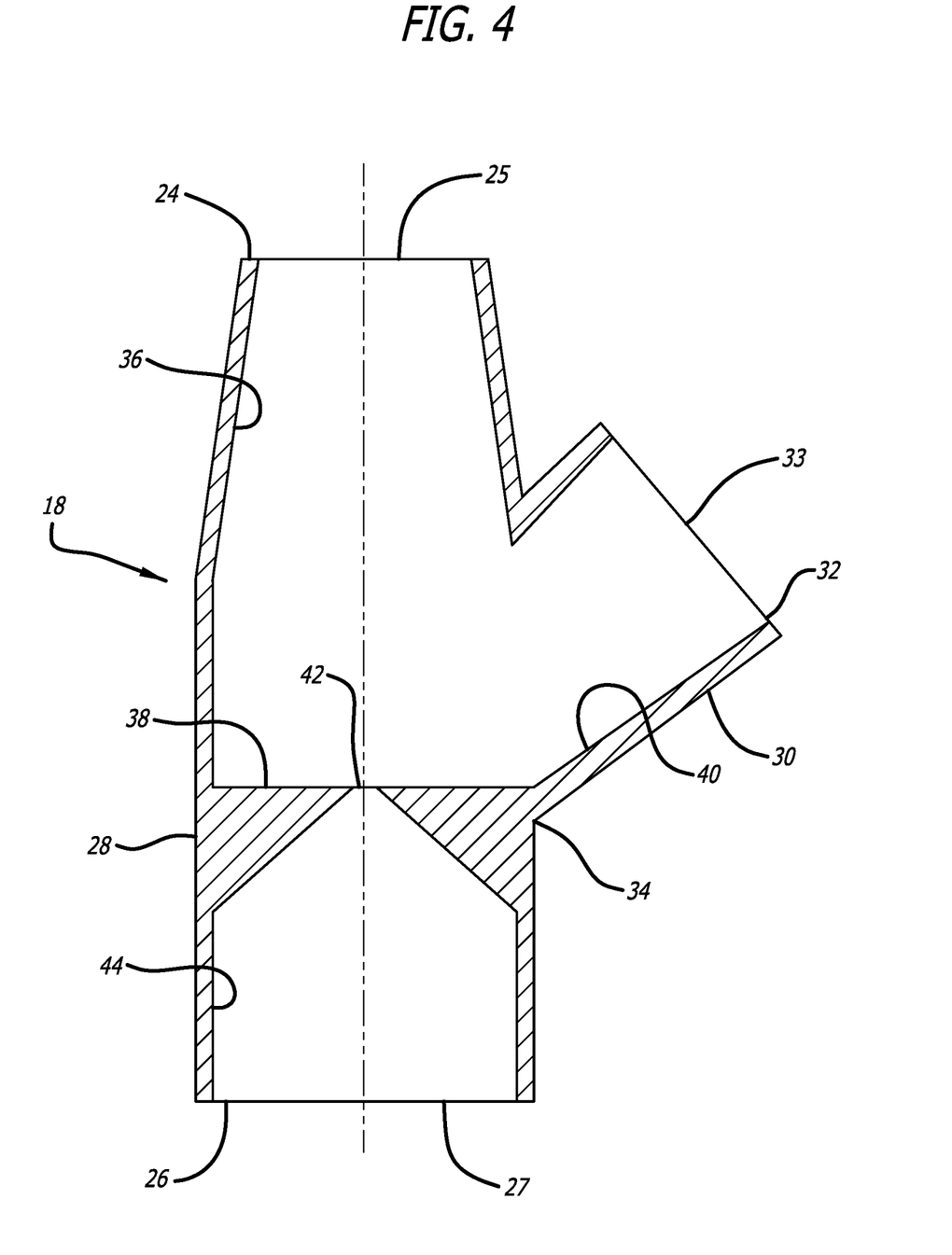
FIG. 4 is a cross-section view taken along lines 4-4 of the resuscitation training device of FIG. 3 depicting the orifice plate and metering orifice.
Figure 5:
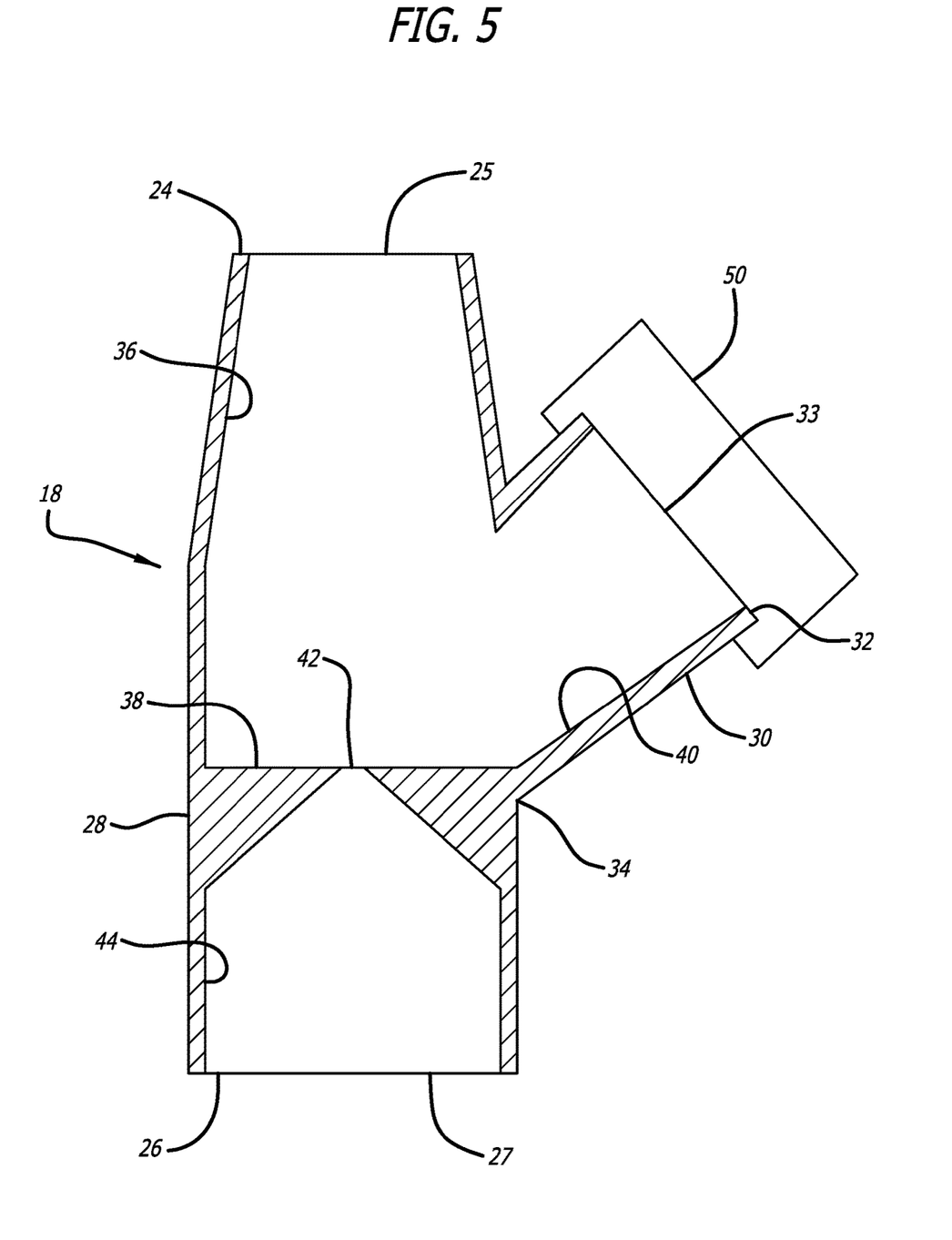
FIG. 5 is a schematic cross-section view of the resuscitation training device of FIG. 3 depicting the orifice plate and metering orifice.
Figure 6:
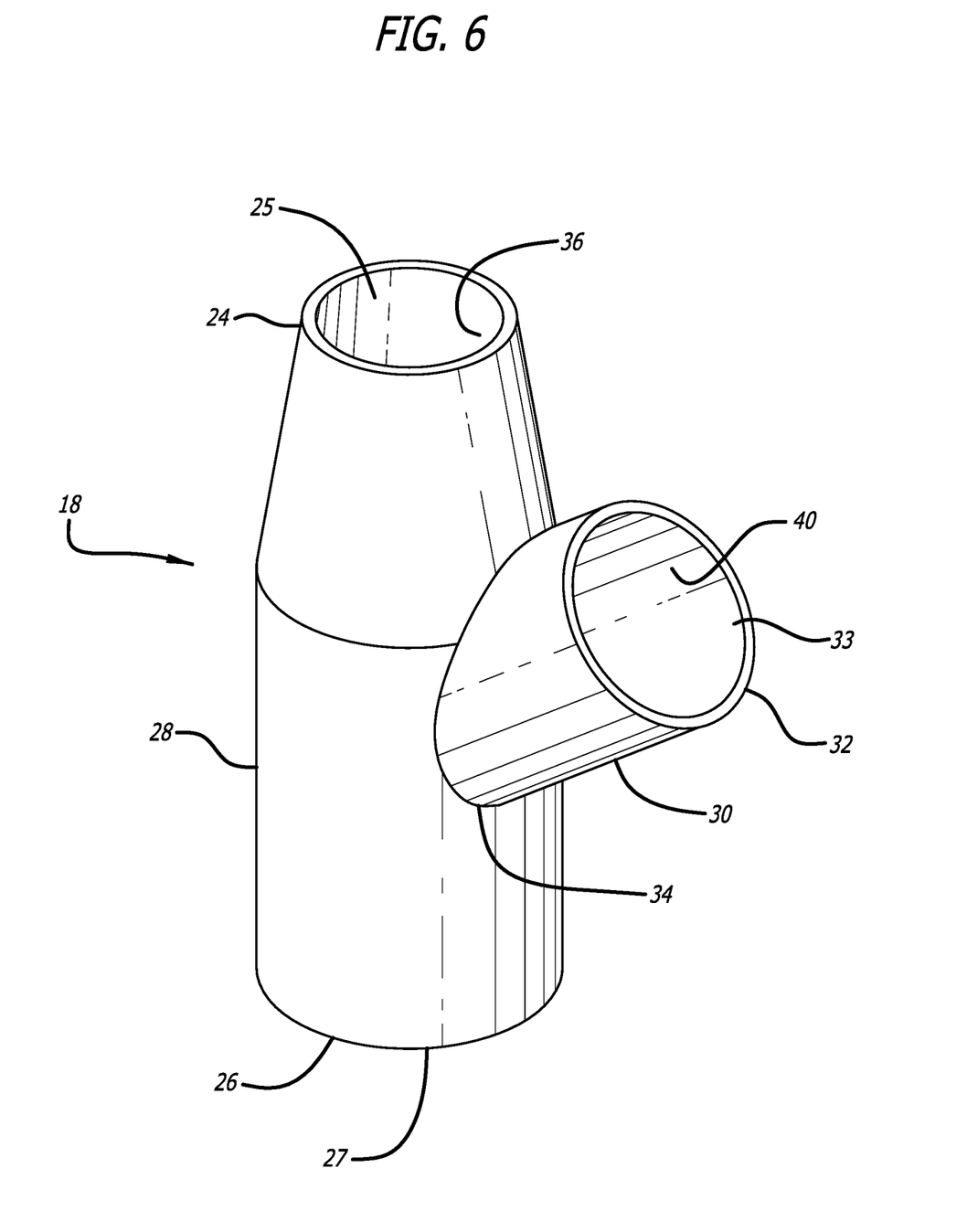
FIG. 6 is a schematic view of the resuscitation training device depicting the second tubular member attached to the first tubular member.
Figure 7:
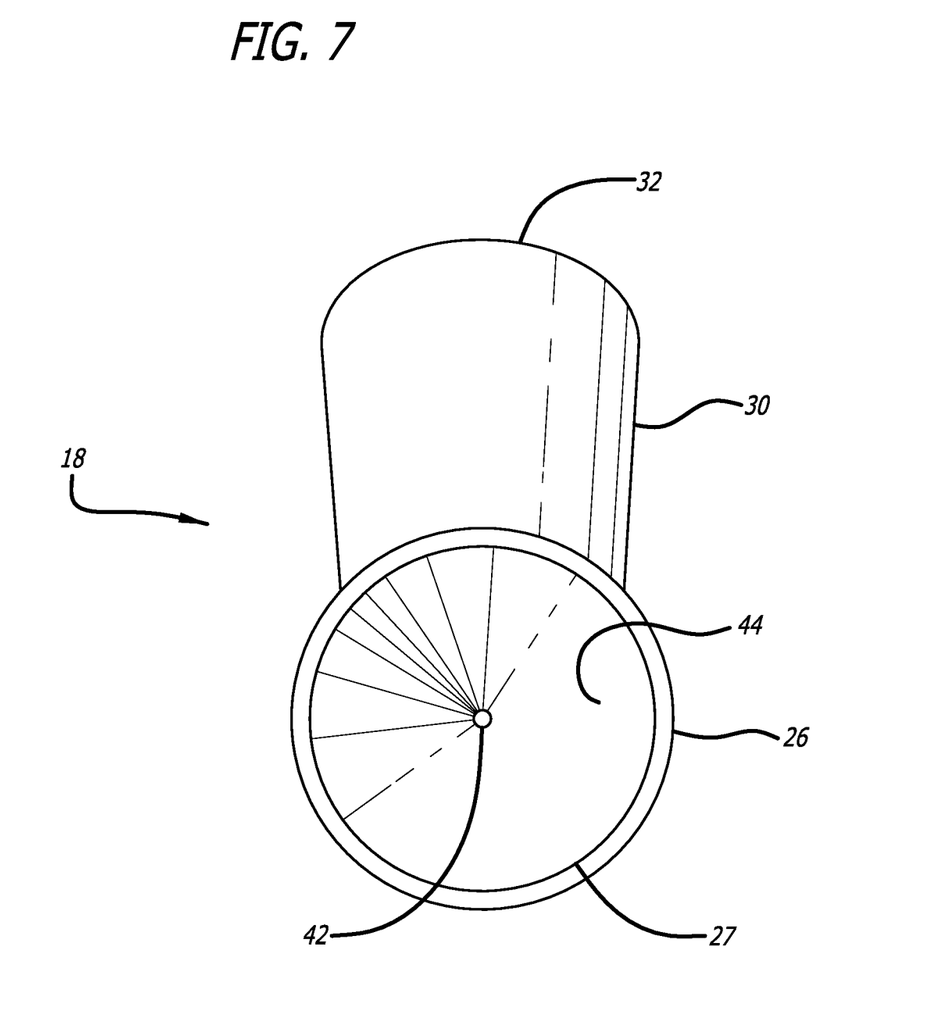
FIG. 7 is a top view of the resuscitation training device depicting the orifice plate and the orifice.

In another embodiment, as shown in FIGS. 1-7, a resuscitation training assembly 18 includes an air delivery ventilation device 10, such as a BVM 12, a pocket mask, a face shield, an endotracheal tube, a resuscitator, and a ventilator. In this embodiment, a first tubular member 22 has a first end 24 and a second end 26 and a tubular body 28 that extends between the first end 22 and the second end 24. A second tubular member 30 has a first end 32 and a second end 34, whereby the second end 34 is attached to the tubular body 28 of the first tubular member 22. The first end 24 of the first tubular member 22 is attached to the air delivery ventilation device 10. A first lumen 36 extends from the first end 24 of the first tubular member 22 to an orifice plate 38 and a second lumen 40 extends through the second tubular member 30 and is in fluid communication with the first lumen 36. A metering orifice 42 extends through the orifice plate 38, and is in fluid communication with the first lumen 36 and the second lumen 40. There is a third lumen 44 extending from the metering orifice 42 to the second end 26 of the first tubular member 22. As shown in FIG. 5, a pressure sensing device 50 is attached to the second tubular member 30. The first tubular member 22 is attached to the air delivery ventilation device 10 so that when a person uses the air delivery ventilation device to deliver air, the pressure sensing device 50 provides instantaneous feedback to the person to determine if there is a proper seal between the air delivery ventilation device 10 and the human patient or training manikin. The first end 24 of the first tubular member 22 comprises an air inlet 25 that is removably attached to the valve 13 using any type of air tight connection (e.g., an adapter fitting having a variable diameter that can be used with any air delivery ventilation device). Alternatively, an air tight seal can be formed by wrapping silicone adhesive tape that is pliable around the joint, providing an air tight seal, and it is easily removable. The second end 26 of the first tubular member 22 comprises an air outlet 27 that is removably attached to the mask 14, again using any suitable type of air tight connection. The first end 32 of the second tubular member 30 is comprises an air outlet 33 that removably attached to the pressure sensing device 50 (e.g., balloon 20). The pressure sensing device 50 provides instantaneous manual, analog or digital feedback to determine whether there is a proper seal between the mask 14 and the live training subject or a training manikin. The diameter of the metering orifice can vary in order to match the sensitivity of the pressure sensing device. By way of example, the diameter of the metering orifice can range from 0.039 inch to 0.24 inch (1 mm to 6 mm), depending on the type of pressuring sensing device being used. The metering orifice diameter can even change with the use of different balloons having different elasticities.

The method of use of the resuscitation training device is describe with reference to FIGS. 1-7. The air inlet 25 will receive air from the operator via the operator's own breath or from the attached air delivery ventilation device 10 (e.g., squeezing the air bag 16 on a BVM 12). Air will enter the first lumen 36 of the first tubular member 22 and have two outlets for the air flow, namely the air outlet 33 removably attached to the balloon 20 or the air outlet 27 removably attached to the mask 14. If the operator has made a proper seal between the mask 14 and the patient's face, then because of the restrictive nature of the metering orifice 42, pressure will build in the first lumen 36 and the second lumen 40, and seek the path of least resistance in the second lumen 40 and out through air outlet 33 and inflate the balloon 20. If the seal between the mask 14 and the patients' face is improper, air will escape around the mask at the patient's face and escape into the environment, and balloon 20 will not inflate because there will be no buildup of air pressure in the first lumen 36 and the second lumen 40. As a result, the operator receives instant feedback and can adjust the mask on the training patient and repeat the training exercise. Repeated training sessions will provide the operator with enough experience to effectively make a proper seal with a BVM 12 (or other air delivery ventilation device 10) the first time that operator needs to use the BVM in an emergency situation. After the training sessions, the resuscitation training device is detached from the BVM 12 (or air delivery ventilation device 10) so that the BVM 12 can be used on live patients.

The resuscitation training device can be formed of a durable plastic material that is injection molded or formed on a 3D printer. Alternatively, the device can be formed from other materials including metallic alloys such as stainless steel, titanium, and cobalt-chromium, as examples. The resuscitation training device also can be made of softer plastic materials such as silicone in order to enhance a better seal with the attachment to the mask and the valve. It is contemplated that the resuscitation training device be formed as a unitary structure, however, it is envisioned that the component parts can be formed and attached together to form the device.

I claim:

1. A resuscitation training device, comprising:
   a mask attachable to a live training subject or attached to a training manikin;
   a first tubular member having a first end and a second end and a tubular body extending between the first end and the second end;
   an air delivery device connected to the first end of the first tubular member;
   a second tubular member having a first end and a second end, the second end being attached to the tubular body of the first tubular member;
   a pressure sensing device connected to the first end of the second tubular member;
   a first lumen extending from the first end of the first tubular member to an orifice plate and a second lumen extending through the second tubular member and in fluid communication with the first lumen;
   a metering orifice on the orifice plate, the metering orifice being in fluid communication with the first lumen and the second lumen;
   a third lumen extending from the metering orifice to the second end of the first tubular member; and
   wherein if the mask is properly attached to the live training subject or the training manikin, air will flow from the air delivery device into the first lumen and into the second lumen and out through the second lumen into the pressure sensing device, with the metering orifice generally resisting flow through the metering orifice.

2. The resuscitation training device of claim 1, wherein the metering orifice has a diameter in the range from 0.039 inch to 0.24 inch.

3. The resuscitation training device of claim 2, wherein the first end of the first tubular member comprises an air inlet and the second end of the first tubular member comprises an air outlet.

4. The resuscitation training device of claim 3, wherein the first end of the second tubular member comprises an air outlet.

5. The resuscitation training device of claim 4, wherein an adapter fitting is attached to the first end of the first tubular member so that the resuscitation training device can be used with different types of air delivery devices.

6. The resuscitation training device of claim 5, wherein the air delivery device includes any of a bag valve mask (BVM), a pocket mask, a face shield, an endotracheal tube, a resuscitator, and a ventilator.

7. The resuscitation training device of claim 6, wherein the air inlet on the first end of the first tubular member is attached to any of the BVM, the pocket mask, the face shield, the endotracheal tube, the resuscitator, and the ventilator.

8. The resuscitation training device of claim 7, wherein the air outlet on the first end of the second tubular member is attached to the pressure sensing device.

9. The resuscitation training device of claim 8, wherein the pressure sensing device provides manual, analog, or digital feedback.

10. A resuscitation training assembly, comprising:
    an air delivery ventilation device;
    a mask attachable to a human patient or attached to a training manikin;
    a first tubular member having a first end and a second end and a tubular body extending between the first end and the second end;
    the air delivery ventilation device connected to the first end of the first tubular member;
    a second tubular member having a first end and a second end, the second end being attached to the tubular body of the first tubular member;
    a first lumen extending from the first end of the first tubular member to an orifice plate and a second lumen extending through the second tubular member and in fluid communication with the first lumen;
    a metering orifice on the orifice plate, the metering orifice being in fluid communication with the first lumen and the second lumen;
    a third lumen extending from the metering orifice to the second end of the first tubular member;
    a pressure sensing device attached to the first end of the second tubular member;
    wherein if the mask is properly attached to the human patient or the training manikin, the air delivery ventilation device will deliver air into the first lumen, through the second lumen and out through an air outlet at the first end of the second tubular member and into the pressure sensing device so that the pressure sensing device provides feedback to determine if there is a proper seal between the mask and the human patient or the training manikin; and wherein when the air delivery ventilation device is delivering air through the air outlet and into the pressure sensing device the metering orifice generally resists flow through the metering orifice.

11. The resuscitation training device of claim 10, wherein the metering orifice has a diameter in the range from 0.039 inch to 0.24 inch.

12. The resuscitation training assembly of claim 11, wherein the first end of first tubular member comprises an air inlet and the second end of the first tubular member comprises an air outlet.

13. The resuscitation training assembly of claim 12, wherein the second end of the first tubular member has a diameter that is greater than a diameter of an outlet connection point on the air delivery ventilation device.

14. The resuscitation training assembly of claim 13, wherein an adapter fitting is attached to the first end of the first tubular member so that the resuscitation training assembly can be used with different types of air delivery ventilation devices.

15. The resuscitation training assembly of claim 14, wherein the air delivery ventilation device includes any of a bag valve mask (BVM), a pocket mask, a face shield, an endotracheal tube, a resuscitator, and a ventilator.

16. The resuscitation training assembly of claim 15, wherein the air inlet on the first end of the first tubular member is attached to any of the BVM, the pocket mask, the face shield, the endotracheal tube, the resuscitator, and the ventilator.

17. The resuscitation training assembly of claim 16, wherein the air outlet on the first end of the second tubular member is attached to the pressure sensing device.

18. The resuscitation training assembly of claim 17, wherein the pressure sensing device provides manual, analog, or digital feedback.

19. The resuscitation training assembly of claim 10, wherein the pressure sensing device is an expandable elastic member.

20. The resuscitation training assembly of claim 19, wherein the expandable elastic member is a balloon.

* * * * *